United States Patent [19]

Kuroda et al.

[11] 4,254,662

[45] Mar. 10, 1981

[54] MULTIPLE ACOUSTIC BEAMFORMER STEP SCANNER

[75] Inventors: Masao Kuroda, Tokyo; Sekijyuro Ono, Hamuramachi; Kageyoshi Katakura, Tokyo; Toshio Kondo, Kunitachi, all of Japan

[73] Assignee: Hitachi Medical Corporation, Tokyo, Japan

[21] Appl. No.: 936,523

[22] Filed: Aug. 24, 1978

[30] Foreign Application Priority Data

Sep. 2, 1977 [JP] Japan .................. 52-105678

[51] Int. Cl.³ ............................................ G01N 29/00
[52] U.S. Cl. ...................................... 73/626; 128/660
[58] Field of Search .................................. 128/660–663; 73/618–626; 340/1 R, 1 SH; 367/11, 103, 105, 123

[56] References Cited

U.S. PATENT DOCUMENTS

| 3,919,683 | 11/1975 | Itamura et al. | 340/1 R |
|---|---|---|---|
| 3,950,723 | 4/1976 | Gilmour | 367/123 |
| 4,064,741 | 12/1977 | Reynolds | 73/626 |
| 4,070,642 | 1/1978 | Iinuma et al. | 340/1 R |
| 4,135,140 | 1/1979 | Buchner | 340/1 R |
| 4,136,325 | 1/1979 | Takamizawa et al. | 73/626 |
| 4,159,462 | 6/1979 | Rocha et al. | 128/661 |
| 4,161,121 | 7/1979 | Zitelli et al. | 73/626 |

OTHER PUBLICATIONS

Ueda, M. et al., "Dynamic Focussing UTS Transducers Using Analog Switch Phase Shifters", Elec. & Comm. in Japan, vol. 58-A, No. 12, (1976, Dec.).

Primary Examiner—Robert W. Michell
Assistant Examiner—Francis J. Jaworski
Attorney, Agent, or Firm—Craig and Antonelli

[57] ABSTRACT

In an ultrasonic imaging system including an array of ultrasonic oscillators, ultrasonic beams are electronically scanned by sequentially selecting a plurality of oscillator sets for beam transmission and reception. For one transmission of ultrasonic waves, at least two receiver oscillator sets having at least some oscillators in common are simultaneously selected, and the respective outputs from the oscillators in the at least two receiver oscillator sets are phase-adjusted so that echoes received by the at least two receiver oscillator sets effectively correspond to echoes substantially emanating from at least two respective different points on a depth level distanced from the plane of the oscillator array by a predetermined depth, whereby at least two signals and hence at least two successive scan lines relating to the echoes from those respective different points are produced. As a result, improved line resolution and rapid line acquisition can be obtained.

15 Claims, 5 Drawing Figures

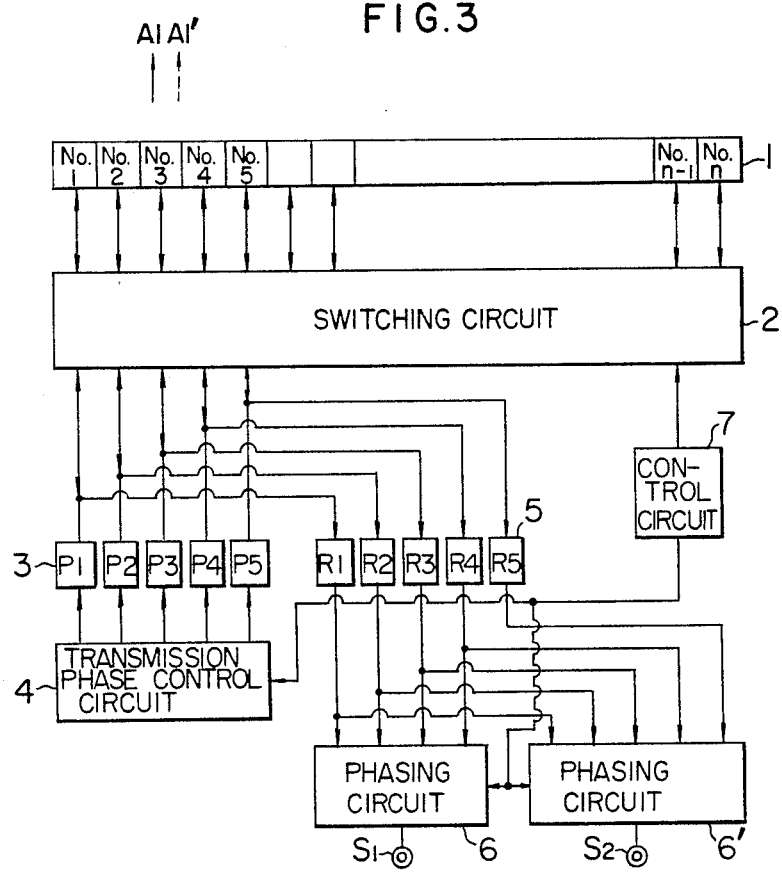
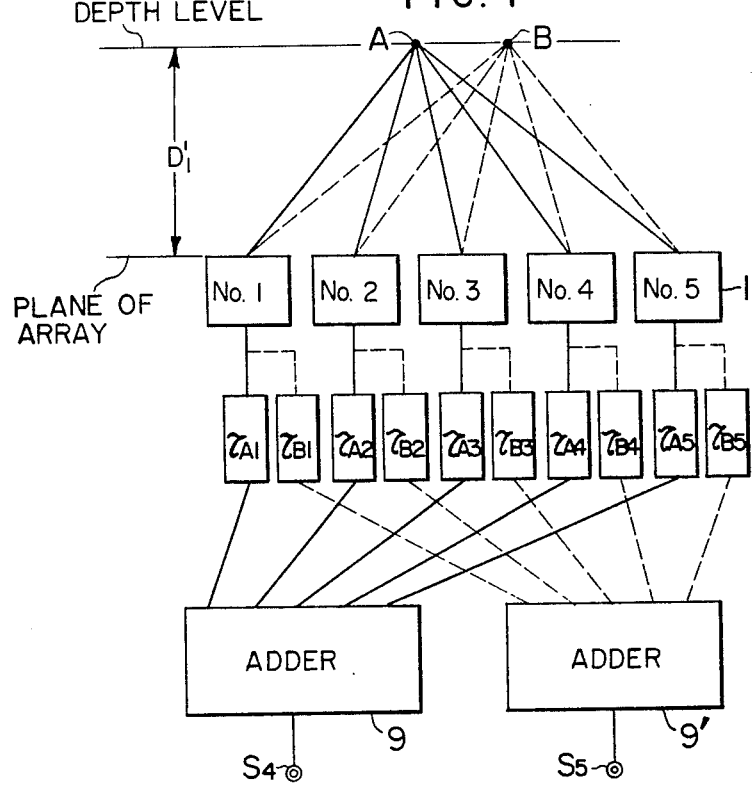

MULTIPLE ACOUSTIC BEAMFORMER STEP SCANNER

This invention relates to an ultrasonic imaging system, and more particularly to such a system in which the time required for the completion of imaging is shortened.

In a certain type of an ultrasonic imaging system for obtaining a two-dimensional image, a beam of ultrasonic waves is electronically scanned to perform a high-speed imaging. In the electronic scan type system, the scanning time can be made shorter in comparison with a mechanical scan type system and it is possible to observe a two-dimensional image in real time. Due to the limit of the velocity of ultrasonic wave, however, the real-time image representation cannot always cover a satisfactory scanning area and be composed of a satisfactory number of scanning lines. In the case where an ultrasonic diagnosing apparatus utilizing the reflection of ultrasonic waves or echoes is operated, for example, a tomographic image is formed by the signals of ultrasonic waves reflected at the depth of 20 cm in a human body. Since the ultrasonic wave has a velocity of about 1.5 mm/$\mu$sec through the human body, the time between the instant of the emission of one ultrasonic wave beam and the instant of the reception of the reflected wave beam equals $200 \times 2/1.5 = 267$ $\mu$sec. If an interrupted time of 33 $\mu$sec is provided until the emission of the next beam, the period of cycle of the emission of the beam equals 300 $\mu$sec. Accordingly, when 200 beams are emitted in slightly different directions, it takes 300 $\mu$sec $\times 200 = 60$ msec. to obtain a two-dimensional image related to those directions and the associated depths. Namely, about 17 frames are scanned per second, which causes flickering on a display in real-time observation. Thus, according to the conventional system, the imaging completion time is restricted even for the scan composed of only 200 scanning lines.

This invention as well as the prior art will be described in conjunction with the accompanying drawings, in which:

FIG. 3 shows in block diagram an embodiment of an ultrasonic imaging system according to this invention;

Figure 5:
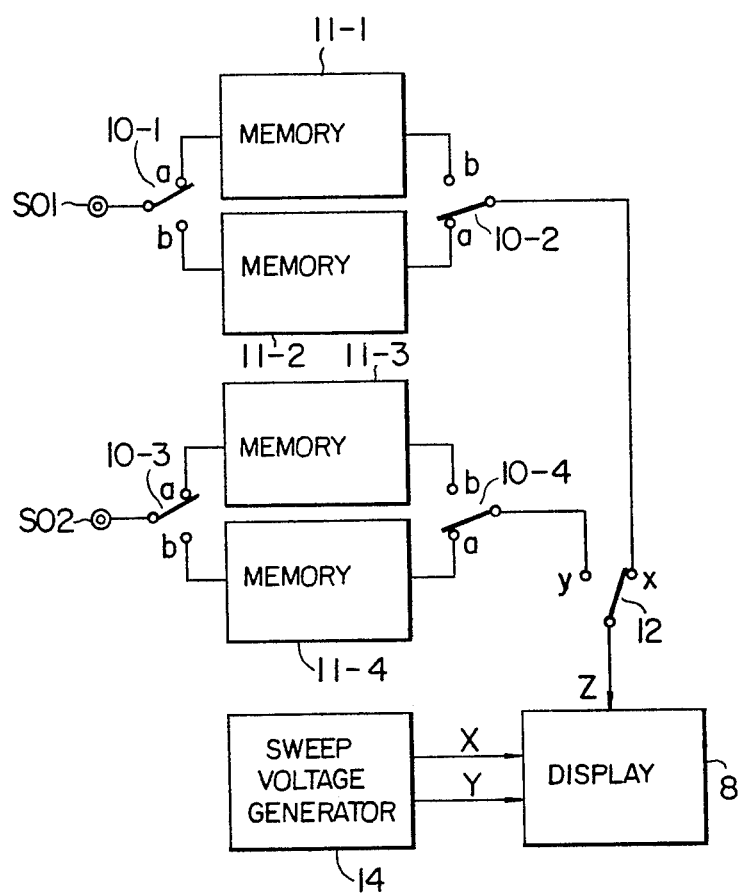

FIG. 4 schematically shows another example of a phasing circuit arrangement as shown in FIG. 3; and FIG. 5 shows an example of a display arrangement.

Figure 1:
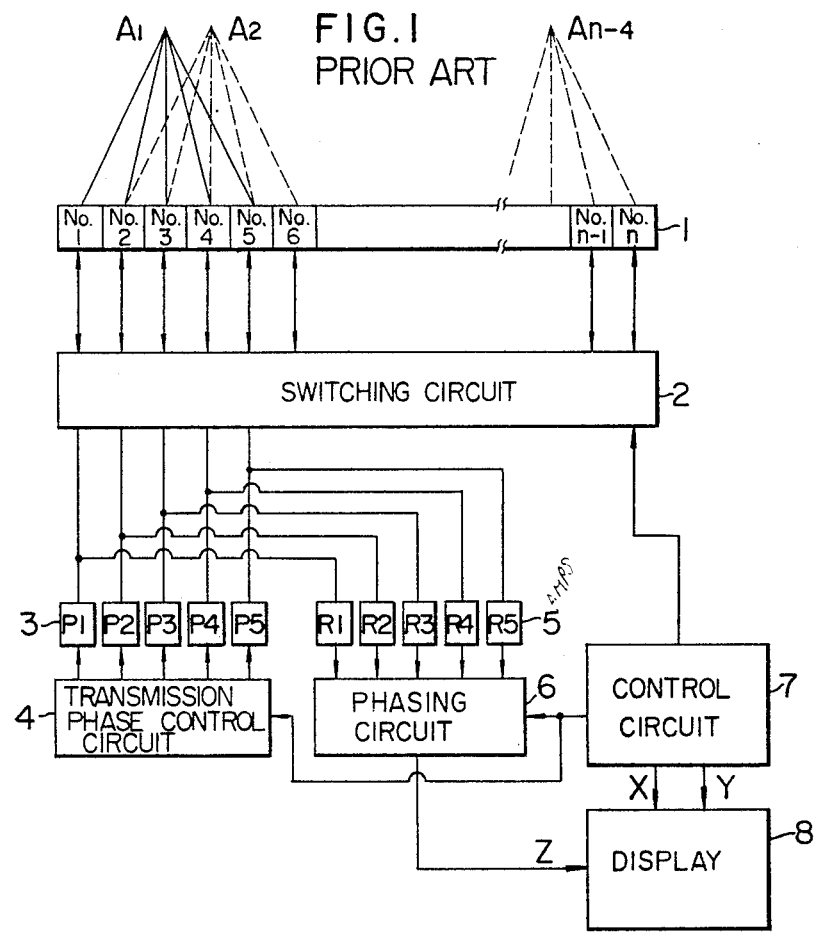
FIG. 1 shows in block diagram a conventional linear electronic scan type ultrasonic imaging system.

Referring to FIG. 1 showing a conventional linear electronic scan type ultrasonic imaging system, a transducer 1 includes an array of n ultrasonic oscillators No. 1—No. n and the oscillators are connected with a switching circuit 2. The switching circuit 2 serves to select k oscillators (k=5 in FIG. 1) successively from among the n oscillators and to connect the selected oscillators with pulsers 3 ($P_1$-$P_5$) which excite the selected oscillators to cause the transmission of ultrasonic waves therefrom and amplifiers 5 ($R_1$-$R_5$) which amplify signals relating to echoes of the transmitted waves. The pulsers 3 are connected with a transmission phase control circuit 4 to produce phase-controlled pulses. The outputs of the amplifiers 5 are sent to a phasing circuit 6 for phase-adjusting the amplified signals through the provision of proper time delays. The output of the phasing circuit 6 serves as a brightness modulating signal to a display 8. A control circuit 7 serves to control the whole system and also generates a sweep signal for the display 8.

Now, the operation of the circuit shown in FIG. 1 will be briefly described. For the first scan, the switching circuit 2 operates to connect the oscillators No. 1-No. 5 with both the pulsers $P_1$-$P_5$ and the amplifiers $R_1$-$R_5$. In this case, No. 1-No. 5 have a directivity such that the transmitted beams or reflected waves are focussed on or emanated from a point $A_1$. For the second scan, the oscillators No. 2-No. 6 are connected with the pulsers $P_1$-$P_5$ and the amplifiers $R_1$-$R_5$. In this case, the oscillators No. 2-No. 6 have a directivity such that the transmitted beams or reflected beams are focussed on or imaged from a point $A_2$. In like manner, the focal or emanating point is linearly shifted from $A_1$ to $A_{n-4}$ along the oscillator array 1.

An object of this invention is to eliminate the restriction on the imaging completion time of an electronic scan type ultrasonic imaging system resulting from the limited velocity of ultrasonic wave through a medium.

To that end, this invention is characterized in that, for each transmission of ultrasonic waves, at least two receiver oscillator sets having at least some oscillators in common are simultaneously selected, and the respective outputs from the oscillators in the at least two receiver oscillator sets are phase-adjusted so that echoes received by the at least two receiver oscillator sets effectively correspond to echoes substantially emanating from at least two respective different points on a depth level distanced from the plane of the oscillator array by a predetermined depth, whereby at least two signals and hence at least two successive scan lines relating to the echoes from those respective different points are produced. As a result, improved line resolution and rapid line acquisition can be obtained. The system may be a multiple acoustic beamformer step scanner.

In general, the directivity of an ultrasonic beam in an ultrasonic imaging system is determined by the product of the directivity of a transmitter oscillator set and the directivity of a receiver oscillator set. If the directivity of the transmitter oscillator set is slightly deviated from that of the receiver oscillator set, it is possible to establish as the total directivity an intermediate directivity between the directivities of the transmitter and receiver sets. This is disclosed in, for example, U.S. application Ser. No. 831,137 entitled "Method for Transmission and Reception of Ultrasonic Beams using Ultrasonic Transducer Element Array" filed Sept. 7, 1977 and assigned to the same assignee as the present application. In accordance with this U.S. application, echoes are received by one receiver oscillator set having a directivity different from that of a transmitter oscillator set.

Figure 2:
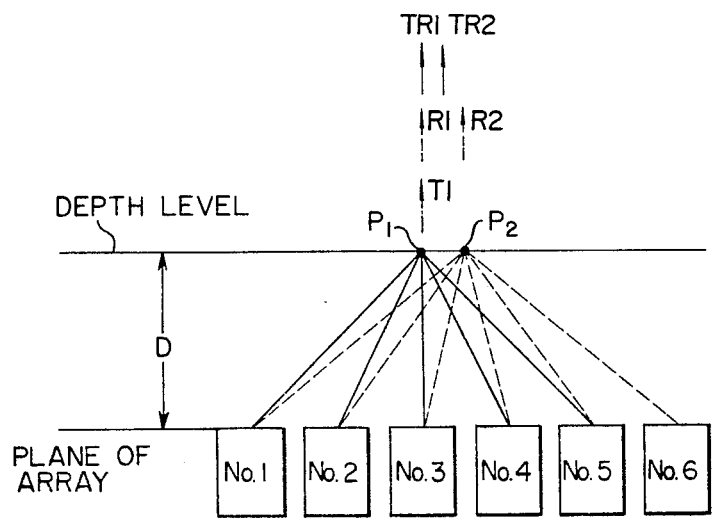
FIG. 2 shows the convergence or divergence of transmitted or reflected ultrasonic waves, which is useful for the explanation of this invention.

It is possible to simultaneously receive echoes by a plurality of receiver sets at least one set of which has a directivity slightly different from that of the transmitter set. This is shown in FIG. 2. When ultrasonic oscillators No. 1-No. 5 are excited, the transmitted ultrasonic beams are directed in the $T_1$ direction along a line passing the center of the oscillators No. 1-No. 5. In such a case, according to one embodiment of this invention, the oscillators No. 1-No. 5 having a reception directivity of the $R_1$ direction and the oscillators No. 1-No. 6 having a reception directivity of the $R_2$ direction are used as receivers for receiving echoes. Accordingly, the resultant or total transmission and reception directivity is the combination of the two directions TR1 and TR2.

Namely, for one transmission of ultrasonic beams, echoes from the two directions TR1 and TR2 can be simultaneously received by the oscillators No. 1–No. 5 and the oscillators No. 1–No. 6, respectively, to produce two successive scan lines. In this way, the imaging completion time which is conventionally restricted due to the velocity of ultrasonic waves can be halved. The respective oscillator outputs are phase-adjusted so that the echoes received by the oscillators No. 1–No. 5 and the oscillators No. 1–No. 6 effectively correspond to echoes substantially emanating from different points $P_1$ and $P_2$ on a depth level distanced from the plane of the oscillator array by a predetermined depth D.

FIG. 3 shows an embodiment of an ultrasonic imaging system according to this invention, in which the simultaneous reception of echoes in two directions is possible. In this embodiment, two phasing circuits 6 and 6' are provided. The phasing circuit 6 is connected with amplifiers $R_1$–$R_4$ which are connected with, for example, oscillators No. 1–No. 4 having a directivity of the direction $A_1$ while the phasing circuit 6' is connected with amplifiers $R_1$–$R_5$ which are connected with, for example, oscillators No. 1–No. 5 having a directivity of the direction $A_1'$. As a result, a signal relating to echoes from the direction $A_1$ and a signal relating to echoes from the direction $A_1'$ are simultaneously obtained at output terminals $S_1$ and $S_2$ of the phasing circuits 6 and 6' respectively. In FIGS. 1 and 3, equal or equivalent components are indicated by the same numerals or symbols. Therefore, the operation of the system shown in FIG. 3 is the same as that of the system shown in FIG. 1, except those of the phasing circuits 6 and 6'.

FIG. 3 shows the case where the number of the oscillators connected with the phasing circuit 6 is different from that of the oscillators connected with the phasing circuit 6'. Alternatively, the different reception directivities can be provided by connecting the same number of the oscillators with each of two delay circuit networks and by controlling the phases of the output signals from the oscillators in the respective delay circuit networks. FIG. 4 shows such a phasing circuit arrangement.

In FIG. 4, oscillators No. 1–No. 5 are connected with a delay circuit network including delay circuits $\tau_{A1}$–$\tau_{A5}$ and with a delay circuit network including delay circuits $\tau_{B1}$–$\tau_{B5}$. The delay circuits $\tau_{A1}$–$\tau_{A5}$ are connected with an adder 9 and the delay circuits $\tau_{B1}$–$\tau_{B5}$ are connected with an adder 9'. In the respective delay circuits $\tau_{A1}$–$\tau_{A5}$ (or $\tau_{B1}$–$\tau_{B5}$) are provided delays corresponding to the differences between the propagation times of echoes from the point A (or B) to the associated oscillators No. 1–No. 5. Namely, the delays are such that all the output signals of the delay circuits $\tau_{A1}$–$\tau_{A5}$ ($\tau_{B1}$–$\tau_{B5}$) connected with the outputs of the oscillators receiving echoes from the point A (or B) have the same phase at input terminals of the adder 9 (or 9'). The points A and B are on a depth level distanced from the plane of the oscillator array by a predetermined depth D'. As a result, a signal relating to echoes from the point A and a signal relating to echoes from the point B are obtained at the output terminal $S_4$ of the adder 9 and at the output terminal $S_5$ of the adder 9'.

FIG. 5 shows an example of the circuit arrangement for displaying signals received simultaneously. The signal S01 sent from the output terminal $S_1$ (see FIG. 3) or $S_4$ (see FIG. 4) is supplied to a memory 11-1 or 11-2 through a switch 10-1. The output of the memory 11-1 or 11-2 is supplied to the Z-axis of the display 8 through switches 10-2 and 12. In like manner, the signal S02 sent from the output terminal $S_2$ (see FIG. 3) or $S_5$ (see FIG. 4) is supplied to a memory 11-3 or 11-4 through a switch 10-3. The output of the memory 11-3 or 11-4 is supplied to the Z-axis of the display 8 through switches 10-4 and 12. Reference numeral 14 indicates a sweep voltage generator for the x- and y-axes of the display 8.

In operation, the switches 10-1~10-4 are first connected with their respective contacts a so that the signals S01 and S02 are stored respectively in the memories 11-1 and 11-3. In this case, the write-in frequency of the memories 11-1 and 11-3 is chosen to be f. After a series of data representing information obtained sequentially at predetermined depths has been stored in the memories 11-1 and 11-3, the switches 10-1~10-4 are connected with their respective contacts b. At the same time, the switch 12 is changed over to select its contact x. While the next coming signals S01 and S02 are stored in the memories 11-2 and 11-4, the previously written content in the memory 11-1 is read therefrom at a read-out frequency 2f equal to twice the write-in frequency f so as to be displayed on the display 8. After the content of the memory 11-1 has been completely read out, the switch 12 is changed over to select its contact y so that the content of the memory 11-3 is read out for displaying on the display 8. When the readout of the content of the memory 11-3 has been finished, the contact x of the switch 12 and the contacts a of the switches 10-1~10-4 are selected so that the content of the memory 11-2 is read out. Thereafter, the contact y of the switch 12 is selected so that the content of the memory 11-4 is read out. Thus, a real-time display can be realized by temporarily storing or writing pieces of information from two directions in the memories for time compression and by alternately reading out them at the read speed equal to twice the write speed.

As described above, according to this invention, echoes having slightly different directivities can be simultaneously received for one transmission of ultrasonic beams. This eliminates the restriction on the imaging completion time resulting from the limited velocity of ultrasonic wave through a medium, so that a fine image with a high density of scanning lines can be observed in real time. It can therefore be said that this invention contributes much to the field of the art.

It is apparent that this invention can be applied equally to the case of the simultaneous reception of echoes having more than two different directivities, though the foregoing description is given exclusively to the simultaneous reception of echoes having two different directivities. Further, though this invention has been described and shown in conjunction with the arrangement in which echoes of ultrasonic waves transmitted from the oscillator array are received by the same array, it should be understood that this invention is applicable to an arrangement in which ultrasonic waves transmitted from a first oscillator array and through an object are received by a second oscillator array disposed opposite to the first oscillator array with respect to the object. In such a case, a second switching circuit similar to the switching circuit 2 of FIG. 3 is associated with the second oscillator array, i.e. the receiver oscillator array and the amplifiers 5 and the phasing circuits 6 and 6' shown in FIG. 3 are associated with the second switching circuit.

We claim:
1. An ultrasonic imaging system comprising an array of plural ultrasonic oscillators adapted to transmit first ultrasonic waves and to receive second ultrasonic waves derived from said first ultrasonic waves, switching means for sequentially selecting for transmission and reception a plurality of oscillator sets in the oscillator array so that at least two receiving oscillator sets having at least some oscillators in common are selected for a single transmission of the first ultrasonic waves to receive the second ultrasonic waves for production of at least two successive scan lines, and phasing means associated with the outputs from the oscillators in each set of said at least two selected receiving oscillator sets for phase-adjusting the respective oscillator output signals so that the second ultrasonic waves received by said at least two selected receiving oscillator sets effectively correspond to ones substantially emanating from at least two respective different points on a depth level distanced from the plane of the oscillator array by a predetermined depth during the single transmission of the first ultrasonic waves, thereby providing at least first and second output signals relating to the second ultrasonic waves from said at least two respective different points to produce said at least two successive scan lines.

2. The system according to claim 1, wherein said phasing means includes a first phasing circuit for applying first predetermined time delays to the output signals from a first set of said selected receiving oscillator sets respectively to provide said first output signal and a second phasing circuit for applying second determined time delays different from said first predetermined time delays to the output signals from a second set of said selected receiving oscillator sets respectively to provide said second output signal, said first and second phasing circuits being associated with said selected oscillator sets respectively so that at least some oscillators to both said circuits are different.

3. The system according to claim 1, wherein each of said receiving oscillator sets for a single transmission of the first ultrasonic waves has the same oscillators, and said phasing means includes first delay circuits for applying first time delays to the output signals from said receiving oscillator sets respectively, second delay circuits for applying second time delays to the output signals from said receiving oscillator sets respectively, a first adder circuit for summing the output signals of said first delay circuits to provide said first output signal, and a second adder circuit for summing the output signals of said second delay circuits to provide said second output signal.

4. An ultrasonic imaging system comprising an array of plural ultrasonic oscillators selectable in sets adapted to transmit first ultrasonic waves and to receive second ultrasonic waves derived from said first ultrasonic waves, switching means for sequentially selecting for transmission and reception a plurality of oscillator sets in the oscillator array so that at least two receiving oscillator sets having at least some oscillators in common are selected for a single transmission of the first ultrasonic waves to receive the second ultrasonic waves for production of at least two successive scan lines, and phasing means associated with the outputs from the oscillators in each set of said at least two selected receiving oscillator sets for phase-adjusting the respective oscillator output signals so that the second ultrasonic waves received by said at least two selected receiving oscillator sets effectively correspond to ones substantially emanating from at least two respective different points on a depth level distanced from the plane of the oscillator array by a predetermined depth during the single transmission of the first ultrasonic waves, thereby providing at least first and second output signals relating to the second ultrasonic waves from said at least two respectively different points to produce said at least two successive scan lines, said phasing means comprising a first phasing circuit for applying first predetermined time delays to the output signals of first selected ones of said oscillators respectively to provide said first output signal and a second phasing circuit for applying second predetermined time delays different from said first predetermined time delays to the output signals of second selected ones of said oscillators respectively to provide said second output signal.

5. An ultrasonic imaging system comprisig an array of plural ultrasonic oscillators selectable in sets adapted to transmit first ultrasonic waves and to receive second ultrasonic waves derived from said first ultrasonic waves, switching means for sequentially selecting for transmission and reception a plurality of oscillator sets in the oscillator array so that at least two receiving oscillator sets having at least some oscillators in common are selected for a single transmission of the first ultrasonic waves to receive the second ultrasonic waves for production of at least two successive scan lines, and phasing means associated with the outputs from the oscillators in each set of said at least two selected receiving oscillator sets for phase-adjusting the respective oscillator output signals so that the second ultrasonic waves received by said at least two selected receiving oscillator sets effectively correspond to ones substantially emanating from at least two respective different points on a depth level distanced from the plane of the oscillator array by a predetermined depth during the single transmission of the first ultrasonic waves, thereby providing at least first and second output signals relating to the second ultrasonic waves from said at least two respectively different points to produce said at least two successive scan lines, said phasing means comprising first delay circuits for applying first time delays to the output signals of said selected oscillators respectively, second delay circuits for applying second time delays to the output signals of said selected oscillators respectively, a first adder circuit for summing the output signals of said first delay circuits to provide said first output signal, and a second adder circuit for summing the output signals of said second delay circuits to provide said second output signal.

6. The system according to claim 1, 2, 3, 5 or 6 further comprising memory means for storing said first and second output signals of said phasing means at a first speed and means for reading out the stored contents of said memory means at a second speed faster than said first speed.

7. The improvement according to claim 4 or 5, further comprising memory means for storing said first and second output signals of said phasing means at a first speed and means for reading out the stored contents of said memory means at a second speed faster than said first speed.

8. The system of claim 1, 4, or 5, wherein the improvement comprises means to control said switching means to select at least two of said sets of said oscillators, at least two of which selected sets differ as to the number of oscillators selected.

9. The system of claim 8, wherein the number of oscillators selected in one of said selected sets differs by the integer one from the number of oscillators selected in the said second selected set.

10. The system of claim 1, 4, or 5, wherein the improvement comprises the feature that the number of inputs received by said phase-adjusting means to produce said first output signal is different from the number of inputs received by said phase-adjusting means to produce said second output signal.

11. The system of claim 10, wherein the number of inputs received by the said phase-adjusting means to produce the said first output signal differs by the integer one from the number of inputs received by said phase-adjusting means to produce the said second output signal.

12. In an ultrasonic imaging system employing an array of plural ultrasonic oscillators, the method comprising:
  transmitting first ultrasonic waves,
  receiving second ultrasonic waves derived from said first ultrasonic waves to produce first and second output signals derived from at least first and second selected oscillator sets having only some oscillators in common,
  adjusting the phase of said first and second output signals, selected from at least said first and second oscillator sets, in relation to each other,
  correlating said first and second output signals to correspond effectively to waves emanating from at least two respective different points on a depth level distanced from the plane of said oscillator array, and
  producing at least two successive scan lines therefrom.

13. In a system as called for in claim 12, comprising the further steps of
  delaying output signals of said first oscillator set to produce said first output signal, and
  delaying output signals of said second oscillator set to produce said second output signal.

14. In a system as called for in claim 13, comprising the further step of
  selecting a number of oscillators in said second selected oscillator set different from the number of oscillators in said first selected oscillator set.

15. In a system as called for in claim 14, wherein the difference between the number of said first oscillators selected and the number of said second oscillators selected is one.

* * * * *